(12) United States Patent
Magalhães Martins

(10) Patent No.: US 12,171,597 B2
(45) Date of Patent: Dec. 24, 2024

(54) DEVICE AND RESPECTIVE METHOD FOR THE ENHANCED DETERMINATION OF A FINE LOCATION OF AT LEAST ONE TRACER WITHIN A BODY PART OF A PATIENT

(71) Applicant: PHYSIBOTICS, LDA, Coimbra (PT)

(72) Inventor: Paulo Jorge Magalhães Martins, Coimbra (PT)

(73) Assignee: PHYSIBOTICS, LDA, Coimbra (PT)

( * ) Notice: Subject to any disclaimer, the term of this patent is extended or adjusted under 35 U.S.C. 154(b) by 315 days.

(21) Appl. No.: 17/768,005

(22) PCT Filed: Oct. 22, 2020

(86) PCT No.: PCT/IB2020/059910
§ 371 (c)(1),
(2) Date: Apr. 11, 2022

(87) PCT Pub. No.: WO2021/079295
PCT Pub. Date: Apr. 29, 2021

(65) Prior Publication Data
US 2023/0077250 A1   Mar. 9, 2023

(30) Foreign Application Priority Data

Oct. 22, 2019   (PT) ......................................... 115858

(51) Int. Cl.
*G06V 10/00* (2022.01)
*A61B 6/00* (2006.01)
*A61B 6/03* (2006.01)

(52) U.S. Cl.
CPC .............. *A61B 6/037* (2013.01); *A61B 6/481* (2013.01)

(58) Field of Classification Search
CPC ........... A61B 6/037; A61B 6/481; A61B 6/02; A61B 6/03; A61B 5/70; G01T 1/2978; G01T 1/161; G01T 1/2985; G06T 11/005
See application file for complete search history.

(56) References Cited

U.S. PATENT DOCUMENTS

| | | | |
|---|---|---|---|
| 5,449,913 A | * | 9/1995 | Chang .................. G01T 1/1611 250/363.04 |
| 6,346,706 B1 | | 2/2002 | Rogers |
| | | | (Continued) |

OTHER PUBLICATIONS

International Search Report of PCT/IB2020/059910 Mailed On Jan. 14, 2021.

*Primary Examiner* — Amir Alavi
(74) *Attorney, Agent, or Firm* — Rivka Friedman

(57) ABSTRACT

The present invention relates to a method and a device for monitoring body parts of a patient simultaneously by means of high-resolution and high-sensitivity detection techniques which detect radiation emitted by a tracer. It is an object of the present invention a device for the enhanced determination of a fine location of at least one tracer within a body part of a patient which comprises a first pair of high-resolution detectors opposing detectors, and a second pair of high-sensitivity detectors and movable opposing detectors, and the device being configured to determine based on signals from the first pair of opposing detectors, position the second pair of opposing detectors based on the coarse location, and determining a fine location of the tracer based on signals from the second pair of opposing detectors, allowing to determine the location of a tracer with high spatial resolution and high sensitivity.

21 Claims, 3 Drawing Sheets

(56) References Cited

U.S. PATENT DOCUMENTS

| | | | | |
|---|---|---|---|---|
| 6,469,306 | B1* | 10/2002 | Van Dulmen | G01T 1/1642 |
| | | | | 250/363.04 |
| 6,967,331 | B2* | 11/2005 | Van Dulmen | G01T 1/1648 |
| | | | | 250/363.04 |
| 7,534,418 | B2* | 5/2009 | Raffel | A61K 51/0406 |
| | | | | 424/9.4 |
| 7,689,269 | B2* | 3/2010 | Thurston | A61B 5/418 |
| | | | | 600/431 |
| 7,720,524 | B2* | 5/2010 | Srinivas | G01T 1/1642 |
| | | | | 600/436 |
| 8,204,285 | B2* | 6/2012 | Fakhri | G06T 5/00 |
| | | | | 382/128 |
| 9,739,898 | B2* | 8/2017 | Hoenk | G01T 1/249 |
| 11,006,911 | B2* | 5/2021 | Liu | A61B 6/4275 |
| 11,058,391 | B2* | 7/2021 | Sun | G01T 7/005 |
| 11,701,067 | B2* | 7/2023 | Vija | A61B 6/469 |
| | | | | 250/363.04 |
| 2004/0251419 | A1 | 12/2004 | Nelson | |
| 2015/0276947 | A1* | 10/2015 | Hoenk | H01L 27/14685 |
| | | | | 250/369 |
| 2018/0000431 | A1 | 1/2018 | Roth et al. | |

* cited by examiner

DEVICE AND RESPECTIVE METHOD FOR THE ENHANCED DETERMINATION OF A FINE LOCATION OF AT LEAST ONE TRACER WITHIN A BODY PART OF A PATIENT

TECHNICAL FIELD OF THE INVENTION

The present invention relates to a method and a device for monitoring several body parts of a patient simultaneously by means of high-resolution and high-sensitivity detection techniques which detect radiation emitted by a tracer, for instance by means of positron emission tomography (PET).

The device and the method according to the present invention may, preferably, be used in the field of nuclear medicine, specifically for determining the location of an injected tracer administered into a patient.

RELATED ART

Positron emission tomography (PET) has a high clinical potential as a functional imaging modality of the patient body. Herein, simultaneous images of the whole-body are, particularly, promising since organs interact among each other. Herein, one or multiple tracers, such as radioactive contrast agents, are injected into the patient body. Those tracers have more affinity to certain cells, which may be located in distant parts of the patient body.

The radioactive tracer emits a positron, which annihilates with an electron of the patient body after a certain range. After annihilation, a pair of back-to-back photons is emitted and eventually exit the patient body. The photon pair is detected by two opposite detectors. For scintillator crystals, there is a certain probability of interaction of the photons with the detectors, which depends on the detector density and atomic number. A high light output and a short decay time are desirable for an optimal signal. For gaseous detectors, such as resistive plate chambers (RPCs), besides the probability of interaction, there is the probability of electron extraction from the resistive material. A compromise between both is desirable for an optimal signal.

Scintillator-based systems are discrete, either in the form of pixelated crystals connected in a one-to-one fashion to photomultipliers (PMTs) or in the form of monolithic crystals readout by several PMTs. RPC-based systems are continuous since the hits position are determined from the charge weight between readout channels and the depth-of-interaction of the hit. The latter detectors are essentially parallax-free and, therefore, perform better in terms of spatial resolution. The former detectors perform better in terms of sensitivity.

Both concepts have been proposed for PET systems with a large axial field-of-view (AFOV). Such systems enable imaging of the whole-body in a single scan with increased sensitivity. This opens the possibility for reducing the dose injected to the patient, decrease the total acquisition time, and tracking the tracer real-time as it travels throughout the patient body.

Scintillator-based systems with a large AFOV are considerably expensive, with the total cost increasing linearly with the number of detectors. RPC-based systems are more cost-effective for such purpose as they are meant to cover large areas. However, their sensitivity is small when compared to Scintillator-based systems.

On the other hand, scintillator crystals suffer from poorer spatial resolution for large acceptance angles as the depth-of-interaction plays a strong role for photons hitting oblique to the detector. However, they are more flexible than RPCs and can assume different geometries in such a way that photons hit them perpendicularly, thus reducing the parallax-effect and improving the spatial resolution.

U.S. Pat. No. 9,632,187 B2 discloses systems and methods for a PET kit. The detector kit may include a gantry, a plurality of PET detector modules, and an event processing device. The PET detector module may include a housing. Such housing may include a connective element configured to removably and adjustably couple the PET detector module to the gantry. The detector module comprises one crystal located within the housing and one light detector configured to detect light by the crystal. The detector module further comprises a communication component configured to communicate data from the at least one light detector to an event processing device to determine coincident events based on received data. The disclosure is also related to a method for adjusting, via the connective element, a position of the PET detector module relative to the first gantry and decoupling the PET detector module relative to the first gantry. The method further comprises the coupling of the PET detector module to a second gantry.

WO 2012/087171 A1 discloses a device for PET with time of flight and whole-body scanning in a single bed position and corresponding readout method. The device comprises at least four detector modules placed around the device axis forming a polygon. The modules comprise resistive plate chambers (RPCs) as gamma photon detectors. Such device further comprises an electronic readout coupled to both ends of the device inside the modules. The disclosure is also related to the readout method.

Paulo Martins, Imaging Techniques in RPC-PET. PHD Thesis, University of Coimbra, 2014, describes a device for PET imaging of small-animals. Such device comprises RPC detectors and a readout system. The thesis also describes a method to determine the fine position of the gamma photon hits in the detectors. A method to reconstruct a full-body image with graphical processing units is also presented. The reconstruction method comprises a time-of-flight-based method for rejection of scattered events in the human body. Clinically relevant reconstruction times were demonstrated.

The present invention provides a cost-effective solution, which yet allows to determine the location of a tracer within the patient body with high spatial resolution and high sensitivity.

SUMMARY OF THE INVENTION

The referred problem is thereby solved by a device and a method for determining the location of a tracer within the patient body as well as a computer program product comprising executable instructions for performing the method according to the subject-matter of the independent claims. Preferred embodiments of the invention, which may be realized in an isolated way or in any arbitrary combination, are disclosed in the dependent claims.

As used in the present specification, the term "comprising" or grammatical variations thereof, are to be taken to specify the presence of stated features, integers, steps or components or groups thereof, but do not preclude the presence or addition of one or more other features, integers, steps, components or groups thereof. The same applies to the term "having" or grammatical variations thereof, which is used as a synonym for the term "comprising".

According to an aspect of the present invention there is provided a device for the enhanced determination of a fine location of at least one tracer within a body—or, in particular, a body part—of a patient The device may comprise a first pair of opposing detectors, the opposing detectors of the first pair consisting of high-resolution detectors and a second pair of opposing detectors, the opposing detectors of the second pair consisting of high-sensitivity detectors and being movable.

In a further aspect, the device may be configured to:
a) obtaining one or more first signals from the first pair of opposing detectors, the one or more first signals comprising spectral information corresponding to radiation emitted by the tracer,
b) determining a coarse location of the tracer based on the one or more first signals,
c) positioning the second pair of opposing detectors based on the determined coarse location,
d) obtaining one or more second signals from the second pair of opposing detectors, the one or more second signals comprising electromagnetic spectral information corresponding to radiation emitted by the tracer,
e) determining a fine location of the tracer based on the one or more second signals.

Accordingly, the device for determining the location of a tracer within the patient body may, preferably, be used for imaging the function of a body part of a patient, wherein the body part of the patient comprises a tumorous tissue. Herein, the tumorous tissue may comprise a tumorous modification which may have been introduced into the tissue of the patient by cancer.

The usage of the first pair of opposing detectors for determining a coarse location and, based on such coarse location, positioning the second pair of opposing detectors and therefrom determining a fine location allows that the number of detectors—in particular detectors providing high-sensitivity—is reduced when compared to prior art solutions.

Alternatively or in addition, the device for determining the location of a tracer within the patient body may also be used for correlating the images-corresponding to signals obtained from the pairs of opposing detectors-obtained from two body parts at the same time.

As indicated above, the present device is used in situations in which the body of the patient undergoes a scan following the injection of a tracer. As used herein, the term "tracer" refers to a radioactive contrast agent, such as 18F-fluorodeoxyglucose (FDG).

According to the present invention, the device comprises at least two pairs of opposing detectors. The term "opposing detectors" refers to detectors that are facing each other with the patient body in between.

In accordance with the present invention, the device comprises detectors with high spatial resolution and detectors with high sensitivity. As used herein, the detectors are designated for determining the gamma radiation as generated by the annihilation of the positrons with the body of the patient. As used herein, the term "detector" refers to an apparatus which is designated for generating a measurable signal from the incident gamma radiation. For this purpose, the measurable signal may, preferably, be selected from an electrical signal, specifically an electrical voltage or an electrical current. In particular, the detector element may be selected from at least two of: resistive plate chambers (RPCs), micro-pattern gaseous detectors (MPGDs), fast timing MPGDs (FTM), gas electron multipliers (GEMs), photomultiplier tubes (PMTs), solid-state single-photon-sensitive devices (silicon photomultipliers; SiPMs), position sensing photomultiplier tubes (PSPMTs), avalanche photodiodes (APDs), charge-coupled devices (CCDs), complementary metal-oxide-semiconductor (CMOS), or quanta image sensor (QIS) chip. However, other kinds of detector elements may also be feasible. It is particularly preferred that the opposing detectors are of the same type and kind in order to increase a comparability of the measured signals between the individual detectors Preferably, the opposing detectors of the first pair are continuous detectors, and the opposing detectors of the second pair are discrete detectors.

In a preferred embodiment, the device may comprise at least one pair of first opposing detectors and/or at least one pair of second opposing detectors. More preferably two, four, eight, twelve, sixteen, twenty or more pairs of first opposing detectors and pairs of second opposing detectors. Herein, each pair of detectors are spaced apart with respect to each other and are, thus, capable of determining with increased spatial resolution the closer they are to the patient body.

In addition, the device may, further, comprise an evaluation device. As generally used, the term "evaluation device" relates to an apparatus which is designated for determining the obtained first and second signals comprising information about the gamma radiation which has been acquired by the first and second pairs of opposing detectors and which may be, specifically, based on the measurable signals being provided by the at first and second pairs of opposing detectors to the evaluation device. For this purpose, a wire-based connection, or, alternatively or in addition, a wireless connection between the first and second pairs of opposing detectors and the evaluation device may be provided.

The evaluation device according to the present invention may, particularly, be designed for determining the tracer location within the body of the patient, wherein this kind of information may be based on the measurable signals which are provided to the evaluation device by the at least two detectors. For this purpose, the evaluation device may comprise a fast analog-to-digital converter, preferably having a sampling rate of 10 ns, more preferably of 4 ns, more preferably of 1 ns or below. Herein, the fast analog-to-digital converter may, preferably, be selected from at least one of: a flash analog-to-digital converter (FADC), a field-programmable gate array (FPGA), an application-specific integrated circuit (ASIC), a versa module eurocard (VME) digitizer, a time readout board (TRB), or an oscilloscope. However, other types of fast analog-to-digital converter may also be conceivable.

In addition, the evaluation device may, further, comprise a clock to assign timestamps to each detector signal and to provide time synchronization of detector signals, preferably having a nanosecond-level or picosecond-level accuracy, more preferably of 100 ps or below.

In addition, the evaluation device may, further, comprise a motion sensor for monitoring motion, such as subject motion. Motion sensors may include monitoring of physiological parameters, such as cardiac and respiratory motion.

In a further aspect of the present invention, a method for the enhanced determination of a fine location of a tracer within a body part of a patient, the tracer emitting radiation, is provided.

The method according to the present invention comprises at least the following steps, wherein, however, additional steps may further be performed. In a preferred embodiment, the indicated steps may be performed in a sequential approach, wherein, however, a subsequent step may at least partially be performed concurrently with a previous step. In an alternatively preferred embodiment, the mentioned steps may be performed in an integrative approach or in a mixed approach by combining the sequential approach and the integrative approach, in particular, for minimizing time and/or storing space required for performing the present method. In addition, further steps which are not indicated here may also be performed.

It will be appreciated that the method of the present invention is implemented by the device of the present invention, in any of its embodiments, the method comprising the steps of:
a) obtaining one or more first signals in turn obtained from the first pair of opposing detectors, the one or more first signals comprising spectral information corresponding to radiation emitted by the tracer,
b) determining a coarse location of the tracer based on the one or more first signals,
c) positioning the second pair of opposing detectors based on the determined coarse location,
d) obtaining one or more second signals from the second pair of opposing detectors, the one or more second signals comprising electromagnetic spectral information corresponding to radiation emitted by the tracer,
e) based on the one or more second signals, determining a fine location of the tracer.

Such method thereby provides that, based on the signals obtained from the first pair of opposing detectors, coarse location is determined and, based on such coarse location, the second pair of opposing detectors are positioned and therefrom a fine location is determined, thus allowing that the number of detectors—in particular detectors providing high-sensitivity—is reduced when compared to prior art solutions.

It is yet an object of the present invention a computer program product comprising executable instructions for performing the method of the present invention, in any of its embodiments.

DESCRIPTION OF THE DRAWINGS

Further optional details and features of the present invention may be derived from the subsequent description of preferred embodiments, preferably in combination with the dependent claims. Therein, the respective features may be realized in an isolated way or in arbitrary combinations. The invention is not restricted to the preferred embodiments. Identical reference numbers in the figures refer to identical elements or to elements having identical or similar functions or to elements corresponding to each other with regard to their functionality.

DETAILED DESCRIPTION

Figure 1:
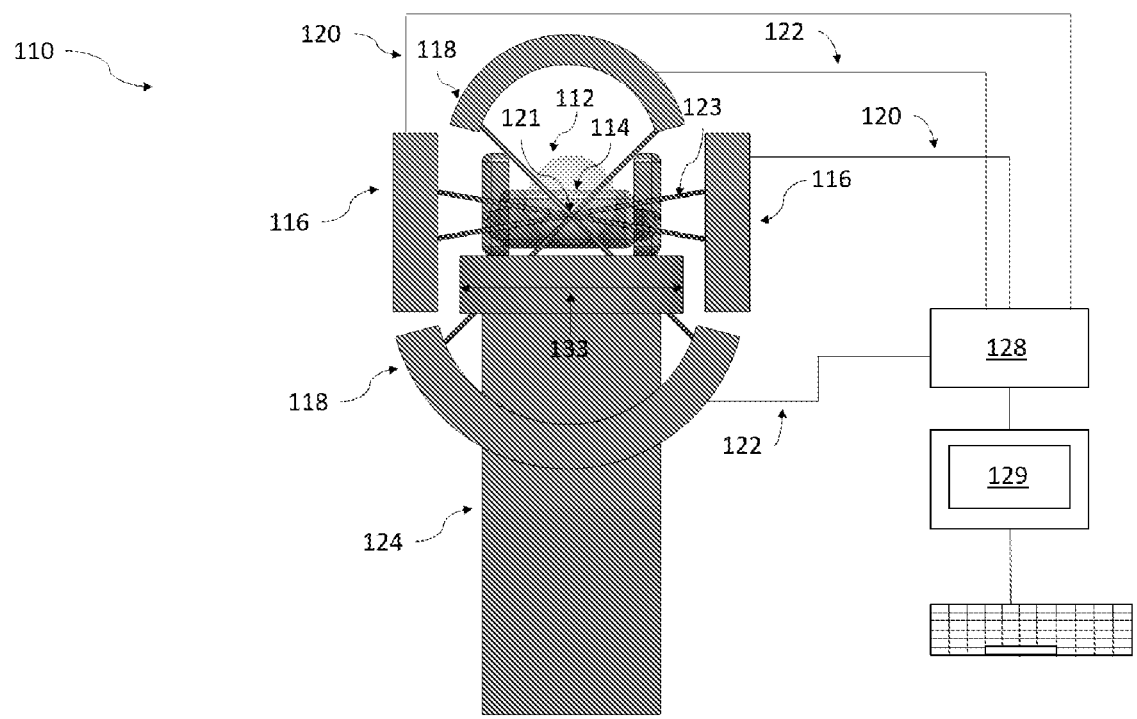
FIG. 1 illustrates a preferred embodiment of a device for determining the location of a tracer within the patient body in accordance with the present invention in a side view, wherein the device comprises two opposing flat detectors with high spatial resolution and two adaptable opposing detectors with high sensitivity.
Figure 2:
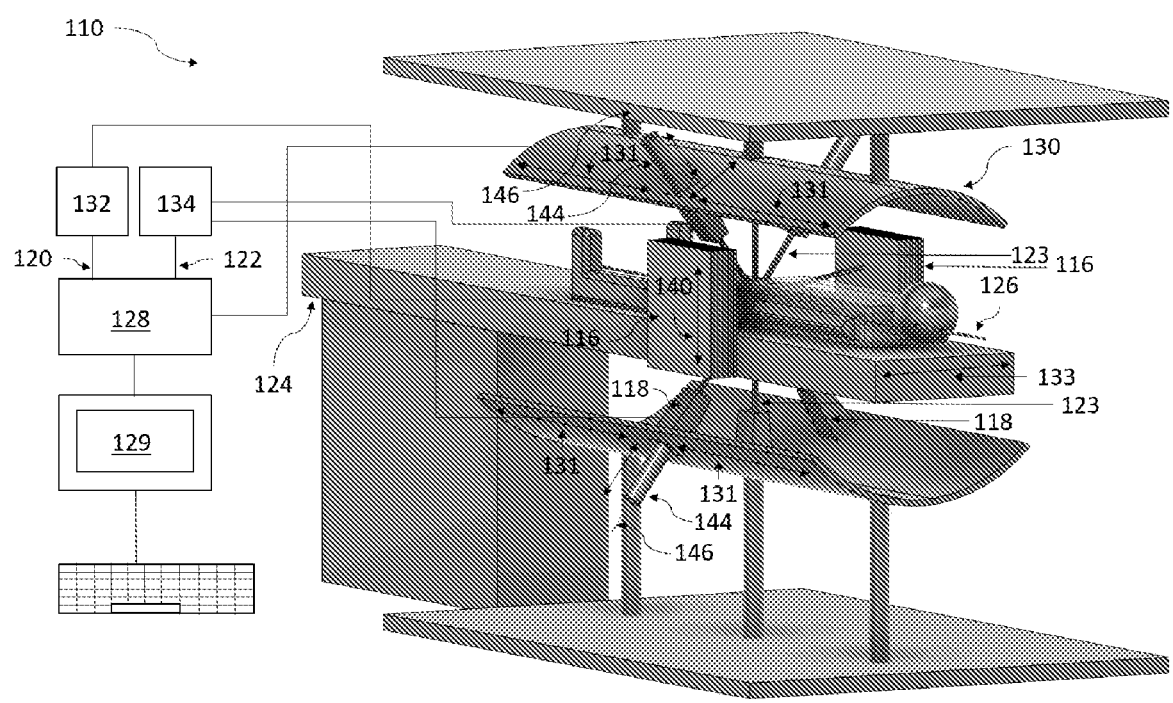
FIG. 2 further illustrates a preferred embodiment of the device for determining the location of a tracer within the patient body in a perspective view, wherein the parallel high-resolution detectors are fixed and the high-sensitivity detectors move by means of a mechanical unit in the axial and horizontal and vertical transaxial directions to the region of interest and may be positioned around an axis crossing the tracer in such a way the gamma rays hit them perpendicularly to their front face. The device further comprises an actuator along a radial axis crossing the coarse location of the tracer such that the distance of the second pair of opposing detectors to the coarse location of the tracer is minimized. The device may further assume a configuration, wherein the whole device is rotated by ±90 degrees, wherein the high-resolution detectors are below and above the patient platform and the high sensitivity detectors move laterally to the patient.
Figure 3:
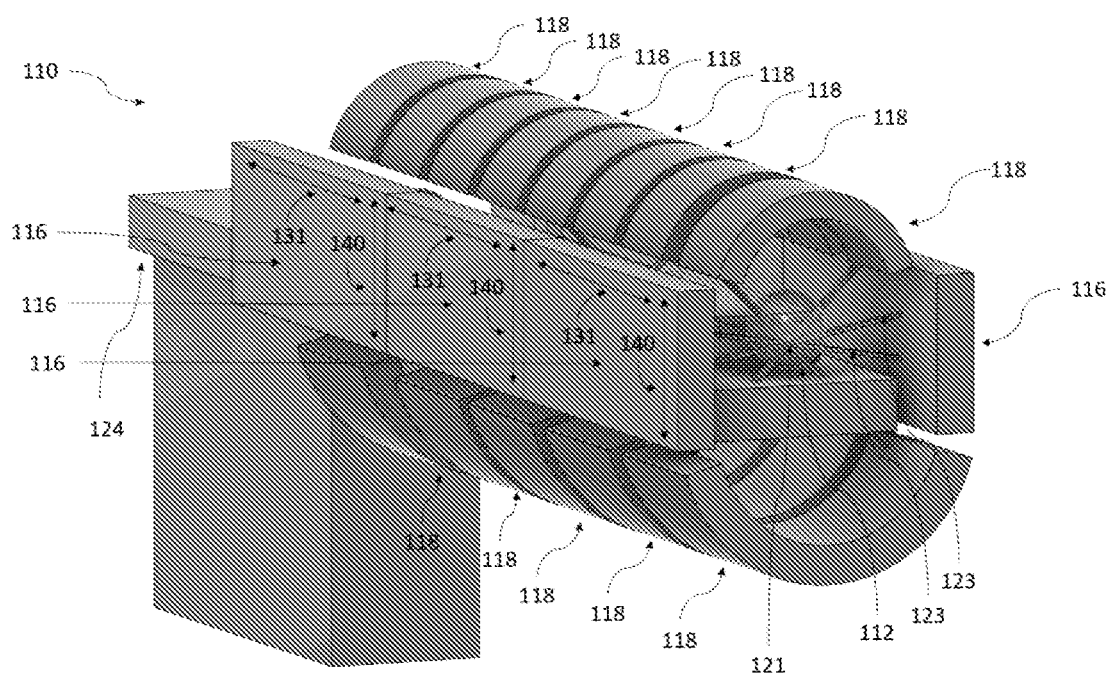
FIG. 3 illustrates a further preferred embodiment of the device for determining the location of a tracer within the patient body in a perspective view, wherein the device comprises a pair of detectors which may be used to image a region of the body (e.g., the brain) and another pair of detectors used to image another region of the body (e.g., the pelvis)
Figure 4:
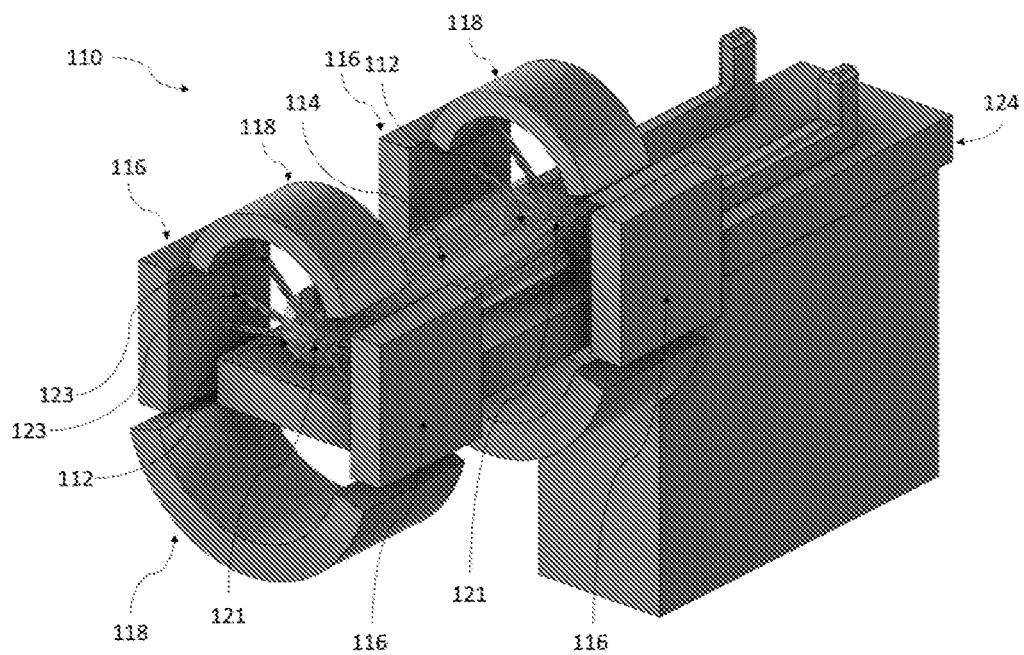
FIG. 4 illustrates a further preferred embodiment of the device for determining the location of a tracer within the patient body in a perspective view, wherein the device comprises a pair of detectors which cover the full body and are able to track the location of the tracer within the body. Once determined the regions of interest, the high-sensitivity detectors move to those regions in order to acquire large statistics.
Figure 5A:
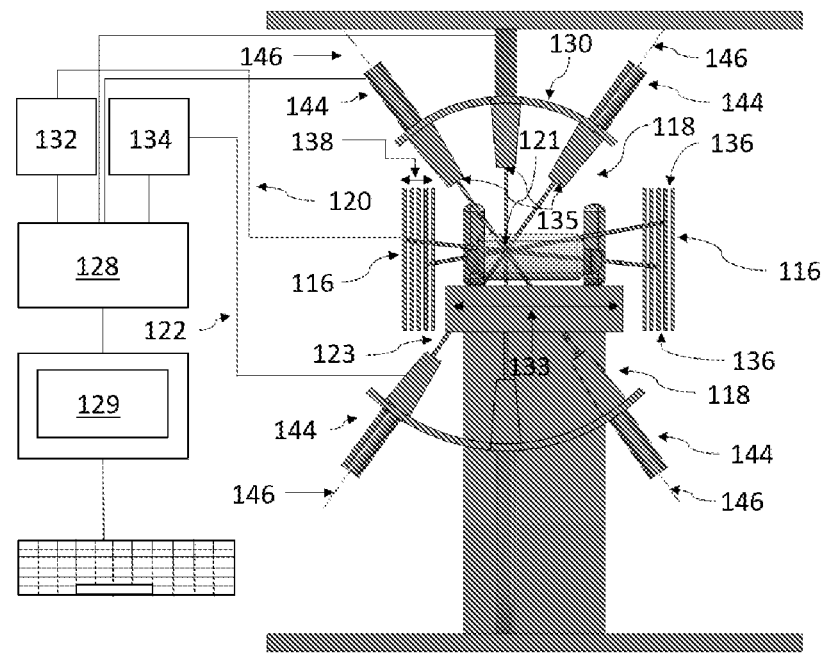
FIGS. 5A and 5B further illustrate the preferred embodiment of a method for determining the location of a tracer within the patient body of FIG. 2 in a side view, wherein the high-sensitivity detectors move between FIGS. 5A and 5B for adjusting the spatial resolution according to the region of interest provided by the parallel high-resolution detectors.
Figure 5B:
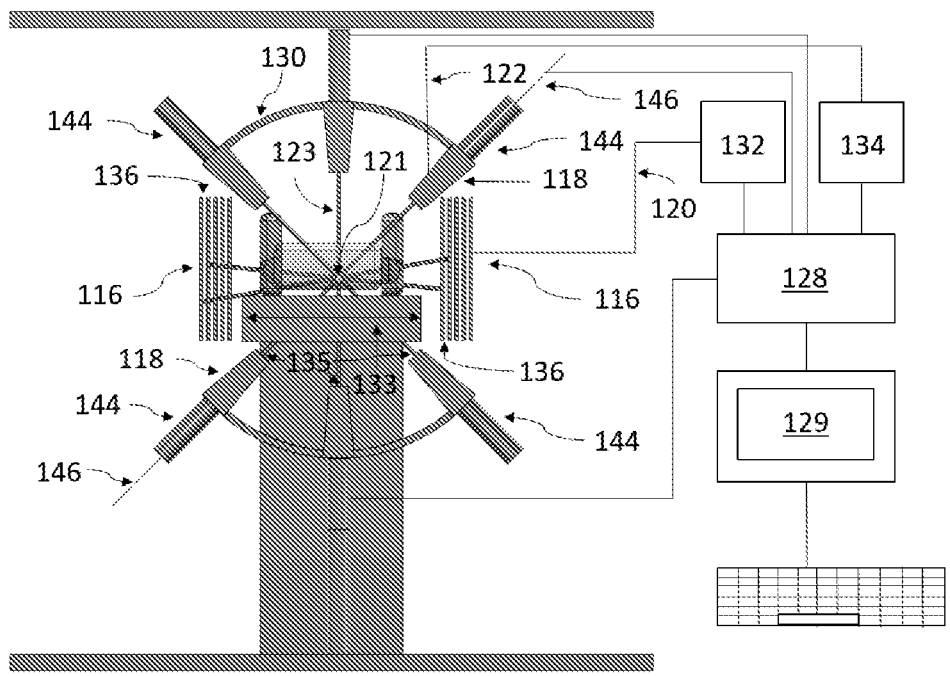

In an embodiment of the device (110) of the present invention, the opposing detectors of the first pair (116) are fixed.

In a further aspect of the device of the present invention, it further comprises a patient platform (124), the patient platform (124) being suitable for receiving a laid patient, and the first pair of opposing detectors and the a second pair of opposing detectors being so positioned that are able to detect radiation (123) emitted by a tracer within a body part (112) of a patient (114) which is laid in the patient platform (124).

In an advantageous embodiment of the device of the present invention, the opposing detectors of the second pair are movable at least around a rotational axis (126) which is parallel to the patient platform (124) and or a plane which is perpendicular to the patient platform (124).

In another advantageous aspect of the device of the present invention, the first pair of opposing detectors (116) and the second pair of opposing detectors (118) and are so positioned that a plane perpendicular to the patient platform (124) intersects both the first pair of opposing detectors (116) and the second pair of opposing detectors (118), thereby allowing an enhanced alignment between detectors.

In a further aspect of the device of the present invention, the first pair of opposing detectors (116) and the second pair of opposing detectors (118) and are so positioned that cover the full patient platform (124) and thereby are able to track the location of the tracer within a whole body of a patient (114).

In a preferred embodiment, the device of the present invention comprises a plurality first pairs of opposing detectors (116) positioned along the patient platform (124) and/or plurality second pairs of opposing detectors (118) positioned along the patient platform (124), thereby allowing to cover a whole body of a patient (114) by being positioned along the patient platform (124), preferably the whole patient platform (124).

In an embodiment of the device of the present invention, to each first pair of opposing detectors (116) corresponds a single second pair of opposing detectors (118).

In an advantageous embodiment of the device of the present invention, to each first pair of opposing detectors (116) corresponds more than one second pair of opposing detectors (118), each first pair (118) having a length such that it covers a section of the patient platform (124) which corresponds to more than one second pair of opposing detectors (116) along a same plane. Such solution allows to reduce the number of first pairs of opposing detectors (116), making use of the continuous condition of such high-resolution detectors.

In an embodiment of the device of the present invention, the first pair of opposing detectors (116) and the second pair of opposing detectors (118) consist of positron emission tomography detectors.

In an advantageous aspect of the device of the present invention, it further comprises an evaluation device (128) which consists of a computational device (129), the evaluation device (128) being configured to determine the coarse location (121) according to step c) and the fine location according to step e).

In an aspect of the device of the present invention, it further comprises a mechanical unit (130), the mechanical unit (130) being configured to move and thereby position the second pair of opposing detectors (118). The evaluation device (128) preferably is further configured to provide the coarse location (121) to the mechanical unit (130) to move and thereby position the second pair of opposing detectors (118). The evaluation device (128), may, further, comprise motion sensors, such sensors being further configured to provide patient motion to the mechanical unit (130) to move and thereby move the second pair of opposing detectors (118) in a synchronous way with the patient motion.

In yet another advantageous aspect of the device of the present invention, it further comprises a first communication module (132) associated with the first pair of opposing detectors (116) and a second communication module (134) associated with the second pair of opposing detectors (118), each of the communication modules being configured to respectively transmit the one or more first signals (120) and the one or more second signals (122) to the evaluation device (128), optionally the communication modules being configured to operate through cabled or wireless communication.

In an inventive aspect of the method of the present invention, step a) comprises determining a detector gap (136) in the horizontal transaxial direction (133) where the radiation was detected in the first pair of opposing detectors (116) and thereby step b) comprises determining the coarse location (121) of an axial (131) and horizontal (133) and vertical (140) transaxial direction of radiation emitted by the tracer hitting the first pair of opposing detectors (116). A disadvantage of scintillator detectors is the absence of depth-of-interaction (DOI). Apart from complex solutions based on multi-crystals organized in two or three layers and algorithms that allow measuring in monolithic scintillator a coarse position of the hit in the transaxial direction, scintillator detectors cannot provide information on the transaxial direction. Moreover, the more oblique the incident photon, the highest the likelihood of depositing energy in more than one detector. This is the so-called parallax effect. Since most detectors have a small pitch (0.25 mm-6 mm), but a large thickness (1 mm-30 mm), the chance that a photon crosses several crystals is higher, the larger the entrance angle of the photon into the detector.

In an additional inventive aspect of the method of the present invention, the positioning of step c) of the second detector is such that the detector is movable along the axial (131) and horizontal (133) and vertical (140) transaxial directions.

In another inventive aspect of the method of the present invention, step e) comprises determining a time difference between radiation and arrival time of radiation emitted by the tracer at each detector of the first pair (116), and reconstructing the one or more second signals with a low-statistics time-of-flight reconstruction routine. The time difference in the arrival time of the photons to the opposing detectors, also called time-of-flight (TOF), limits the so-called line-of-response (LOR) between two detectors to a line segment. TOF thereby is relevant in accelerating the reconstruction routines and increasing the signal-to-noise ratio.

In an aspect of the method of the present invention, the positioning of step c) is such that the detectors of the second pair of opposing detectors (118) are positioned in relation to a rotational axis (126) crossing the coarse location (121) of the tracer such that radiation emitted by the tracer hits the detectors of the second pair of opposing detectors perpendicularly to a front face (135) of such detectors. Events hitting a detector perpendicularly with high resolution and high sensitivity will provide more reliable means of measuring the real activity in the tracer as only the ones emitted from the tracer will be detected.

In another aspect of the method the positioning of step c) is such that the detectors of the second pair of opposing detectors (118) are positioned by means of an actuator (144) along a radial axis (146) crossing the coarse location (121) of the tracer such that the distance of the second pair of opposing detectors (118) to the coarse location (121) of the tracer is minimized and the sensitivity of the second pair of opposing detectors (118) is increased.

In an embodiment, step e) comprises reconstructing the one or more second signals based on the determined coarse location (121) of the tracer with a maximum a posteriori probability (MAP) estimate algorithm. The usage of PET-MR to use the prior knowledge of the fine position of an anatomical structure provided by the MRI and model it in the reconstruction of PET images. That is the so-called maximum a posteriori probability (MAP) estimate. The MAP can be used to obtain a point estimate of an observed quantity on the basis of empirical data. It is similar to the maximum-likelihood (MLEM) algorithms but employs an optimization objective which incorporates a prior distribution over the quantity one wants to estimate. It is seen as a regularization of the MLEM. So far, MAP has not been used in PET data based on prior PET distributions. It is mostly used with a prior MRI distribution. The advantage is that no MRI is needed as the prior knowledge is already offered by the high-resolution detectors. The process can occur iteratively, with the PET distributions from both high-resolution detectors and high-sensitivity detectors feeding each other alternatively In yet another inventive aspect of the method of the present invention, allowing to correlate signals obtained from at least two body parts (112) of a patient (114), it further comprises correlating the location of a tracer at at least two body parts (112) of a patient (114), such correlation comprising:

determining a fine position of the tracer at a given time point during an uptake period within one region of the body, determining the fine position of the tracer at the same time point during an uptake period within another region of the body, measuring a standard uptake value in both regions during a predefined time period, and extracting time correlations between the uptake in both regions.

An associated advantage is the simultaneous spatial tracking of a tracer and its kinetics (activity along time) in different parts of the body. Quantification techniques demand blood sampling as an input to correlate with the activity the brain, heart, tumour, etc. It is therefore an objective of the present invention to evaluate the location and the kinetics of a tracer in different parts of the body simultaneously. The one or several tracers may present different kinetics with higher uptake times in some organs than in others. This could be quantified in a single scan without moving the patient and without blood sampling to estimate the true activity in the body. The metabolism of a tumour can be imaged with FDG, while the myocardium perfusion of the heart is imaged with $^{82}$Rubidium. This is the so-called parametric imaging: several organs monitored at the same time and their uptakes correlated among each other.

In an advantageous aspect of the method of the present invention, it further comprises correlating the location of a tracer within the whole body of a patient (114), such correlation comprising:

determining the fine position of the tracer at a given time point during an uptake period within the whole body of the patient (114), measuring an uptake in the whole body and in a region of interest, and correlating a standard uptake value in the whole body and in a region of interest.

Some tumours are not detected as the normal procedure is to image the body from the eyes to thighs to reduce scanning time. Brain, legs and feet are usually left unscanned. The detection of tumours in such regions provides however assessment of disease progression. A metastasized tumour in a leg from melanoma would change the staging and treatment course. If one could find with an affordable full body scan a tumour in unexpected regions, the second pair of the detectors could confirm and enhance the fine location of that tumour.

Furthermore, unexpected activity in a certain part of the body could trigger the second pair of detectors to move to that region. Let us say we want to evaluate the sexual response of an individual, different parts of the body may get higher uptake, such as the heart, brain, and pelvic region, among others. A whole-body scan would determine the regions of interest and could correlate specific tracers with affinity to that region with a tracer with an affinity to the whole-body metabolism, such as FDG.

In an embodiment a patient could see real-time the functioning of his body, thus mimicking other neurofeedback therapies.

Other modifications and variations will also be apparent to the skilled person.

The invention claimed is:

1. A device (110) for the enhanced determination of a fine location of at least one tracer within a body part (112) of a patient (114) wherein it comprises:

a first pair of opposing detectors (116), the opposing detectors of the first pair consisting of high-resolution detectors, a second pair of opposing detectors (118), the opposing detectors of the second pair consisting of high-sensitivity detectors and being movable, and the device (110) being configured to:

a) obtaining one or more first signals (120) from the first pair of opposing detectors, the one or more first signals comprising spectral information corresponding to radiation (123) emitted by the tracer, b) determining a coarse location (121) of the tracer based on the one or more first signals (120), c) positioning the second pair of opposing detectors (118) based on the determined coarse location (121), d) obtaining one or more second signals (122) from the second pair of opposing detectors (118), the one or more second signals (122) comprising electromagnetic spectral information corresponding to radiation (123) emitted by the tracer, e) determining a fine location of the tracer based on the one or more second signals (122).

2. A device (110) according to claim 1 wherein the opposing detectors of the first pair (116) are fixed.

3. A device (110) according to claim 1 wherein it further comprises a patient platform (124), the patient platform (124) being suitable for receiving a laid patient, and the first pair of opposing detectors 116 and the second pair of opposing detectors being so positioned that are able to detect radiation (123) emitted by a tracer within a body part (112) of a patient (114) which is laid in the patient platform.

4. A device (110) according to claim 3 wherein the opposing detectors of the second pair (118) are movable at least around a rotational axis (126) which is parallel to the patient platform and or a plane which is perpendicular to the patient platform (124).

5. A device (110) according to claim 3 wherein the first pair of opposing detectors (116) and the second pair of opposing detectors (118) and are so positioned that a plane perpendicular to the patient platform (124) intersects both the first pair of opposing detectors (116) and the second pair of opposing detectors (118) wherein, optionally, the first pair of opposing detectors (116) and the second pair of opposing detectors (118) and are so positioned that cover the full patient platform (124) and thereby are able to track the location of the tracer within a whole body of a patient (114).

6. A device (110) according to claim 5 wherein it comprises a plurality first pairs of opposing detectors (116) positioned along the patient platform (116) and/or plurality second pairs of opposing detectors (118) positioned along the patient platform (124), wherein, optionally:

to each first pair of opposing detectors (118) corresponds a single second pair of opposing detectors (116), or to each first pair of opposing detectors (118) corresponds more than one second pair of opposing detectors (116), each first pair (118) having a length such that it covers a section of the patient platform which corresponds to more than one second pair of opposing detectors (116) along a same plane.

7. A device (110) according to claim 1 wherein it further comprises an evaluation device (128) which consists of a computational device (129), the evaluation device being configured to determine the coarse location (121) according to step c) and the fine location according to step e).

8. A device (110) according to claim 7 wherein the evaluation device (128) is further configured to provide the coarse location (121) to the mechanical unit (130) to move in an axial (131) or horizontal (133) or vertical (140) transaxial direction and thereby position the second pair of opposing detectors (118).

9. A device (110) according to claim 7 wherein it further comprises a first communication module (132) associated with the first pair of opposing detectors (116) and a second communication module (134) associated with the second pair of opposing detectors (118), each of the communication modules being configured to respectively transmit the one or more first signals (120) and the one or more second signals (122) to the evaluation device, optionally the communication modules being configured to operate through cabled or wireless communication.

10. A device (110) according to claim 1 wherein it further comprises a mechanical unit (130), the mechanical unit (130) being configured to move in an axial (131) or horizontal (133) or vertical (140) transaxial direction and thereby position the second pair of opposing detectors (118).

11. A device (110) according to claim 1 wherein it comprises at least one pair of first opposing detectors (116) and/or at least one pair of second opposing detectors (118), preferably two, four, eight, twelve, sixteen, twenty or more pairs of first opposing detectors (118) and/or pairs of second opposing detectors (116).

12. A device (110) according to claim 1 wherein the opposing detectors of the first pair (116) are continuous detectors, and the opposing detectors of the second pair (118) are discrete detectors.

13. A device (110) according to claim 1 wherein first pair of opposing detectors (116) and the second pair of opposing detectors (118) consist of positron emission tomography detectors.

14. A method for the enhanced determination of a fine location of a tracer within a body part (112) of a patient (114), the tracer emitting radiation (123), the method being implemented by a device (110), the device (110) being for the enhanced determination of a fine location of at least one tracer within a body part (112) of a patient (114) wherein the device (110) comprises:
- a first pair of opposing detectors (116), the opposing detectors of the first pair consisting of high-resolution detectors,
- a second pair of opposing detectors (118), the opposing detectors of the second pair consisting of high-sensitivity detectors and being movable, and the device (110) being configured to:
- a) obtaining one or more first signals (120) from the first pair of opposing detectors, the one or more first signals comprising spectral information corresponding to radiation (123) emitted by the tracer,
- b) determining a coarse location (121) of the tracer based on the one or more first signals (120),
- c) positioning the second pair of opposing detectors (118) based on the determined coarse location (121),
- d) obtaining one or more second signals (122) from the second pair of opposing detectors (118), the one or more second signals (122) comprising electromagnetic spectral information corresponding to radiation (123) emitted by the tracer,
- e) determining a fine location of the tracer based on the one or more second signals (122), and the method comprising the steps of:
- a) obtaining one or more first signals (120) in turn obtained from the first pair of opposing detectors (116), the one or more first signals (120) comprising spectral information corresponding to radiation (123) emitted by the tracer,
- b) determining a coarse location (121) of the tracer based on the one or more first signals (120),
- c) positioning the second pair of opposing detectors (118) based on the determined coarse location (121),
- d) obtaining one or more second signals (122) from the second pair of opposing detectors (118), the one or more second signals (122) comprising electromagnetic spectral information corresponding to radiation (123) emitted by the tracer,
- e) based on the one or more second signals (122), determining a fine location of the tracer.

15. A method according to claim 14 wherein step a) comprises determining a detector gap (136) in the horizontal transaxial direction (133) where the radiation (123) was detected in the first pair of opposing (116) detectors and thereby step b) comprises determining the coarse location (121) of an axial (131) and horizontal (133) and vertical (140) transaxial direction of radiation (123) emitted by the tracer hitting the first pair of opposing detectors (116), and wherein, optionally, the positioning of step c) of the second detector is such that the detector is movable along the axial (131) and horizontal (133) and vertical (140) transaxial directions, and wherein, optionally, step e) comprises determining a time difference between radiation (123) an arrival time of radiation (123) emitted by the tracer at each detector of the second pair (116), and reconstructing the one or more first signals (116) with a low-statistics time-of-flight reconstruction routine.

16. A method according to claim 15 wherein it further comprises correlating the location of a tracer at least two body parts (112) of a patient (114), such correlation comprising:
- determining a fine position of the tracer at a given time point during an uptake period within one region of the body (112),
- determining the fine position of the tracer at the same time point during an uptake period within another region of the body (112),
- measuring a standard uptake value in both regions during a predefined time period, and
- extracting time correlations between the uptake in both regions.

17. A method according to claim 15 wherein it further comprises correlating the location of a tracer within the whole body of a patient (114), such correlation comprising:
- determining the fine position of the tracer at a given time point during an uptake period within the whole body of the patient (114),
- measuring an uptake in the whole body and in a region of interest, and
- correlating a standard uptake value in the whole body and in a region of interest.

18. A method according to claim 15 wherein the tracer comprises, preferably consists of, 18F-fluorodeoxyglucose (FDG).

19. A method according to claim 14, wherein the positioning of step c) is such that the detectors of the second pair of opposing detectors (118) are positioned in relation to a rotational axis (126) crossing the coarse location (121) of the tracer such that radiation (123) emitted by the tracer hits the detectors of the second pair (118) of opposing detectors perpendicularly to a front face (135) of such detectors.

20. A method according to claim 14, wherein the positioning of step c) is such that the detectors of the second pair of opposing detectors (118) are positioned by means of an actuator (144) along a radial axis (146) crossing the coarse location (121) of the tracer such that the distance of the second pair of opposing detectors (118) to the coarse location (121) of the tracer is minimized and the sensitivity of the second pair of opposing detectors (118) is increased, and wherein, optionally, step e) comprises reconstructing the one or more second signals based (122) on the determined coarse location (121) of the tracer, preferably with a maximum a posteriori probability (MAP) estimate algorithm.

21. A computer program product embodied on a non-transitory computer readable medium comprising executable instructions for performing a method for the enhanced determination of a fine location of a tracer within a body part (112) of a patient (114), the tracer emitting radiation (123), the method being implemented by a device (110), the device (110) being for the enhanced determination of a fine location of at least one tracer within a body part (112) of a patient (114) wherein the device (110) comprises:

a first pair of opposing detectors (116), the opposing detectors of the first pair consisting of high-resolution detectors, a second pair of opposing detectors (118), the opposing detectors of the second pair consisting of high-sensitivity detectors and being movable, and the device (110) being configured to:

a) obtaining one or more first signals (120) from the first pair of opposing detectors, the one or more first signals comprising spectral information corresponding to radiation (123) emitted by the tracer, b) determining a coarse location (121) of the tracer based on the one or more first signals (120), c) positioning the second pair of opposing detectors (118) based on the determined coarse location (121), d) obtaining one or more second signals (122) from the second pair of opposing detectors (118), the one or more second signals (122) comprising electromagnetic spectral information corresponding to radiation (123) emitted by the tracer, e) determining a fine location of the tracer based on the one or more second signals (122), and the method comprising the steps of:

a) obtaining one or more first signals (120) in turn obtained from the first pair of opposing detectors (116), the one or more first signals (120) comprising spectral information corresponding to radiation (123) emitted by the tracer, b) determining a coarse location (121) of the tracer based on the one or more first signals (120), c) positioning the second pair of opposing detectors (118) based on the determined coarse location (121), d) obtaining one or more second signals (122) from the second pair of opposing detectors (118), the one or more second signals (122) comprising electromagnetic spectral information corresponding to radiation (123) emitted by the tracer, e) based on the one or more second signals (122), determining a fine location of the tracer.

* * * * *